(12) United States Patent
Hansen

(10) Patent No.: US 7,566,344 B2
(45) Date of Patent: Jul. 28, 2009

(54) ADJUSTABLE AREOLA AND NIPPLE PROSETHESIS

(76) Inventor: Janice Hansen, 235 W. Benton Ave., Naperville, IL (US) 60540

( * ) Notice: Subject to any disclaimer, the term of this patent is extended or adjusted under 35 U.S.C. 154(b) by 865 days.

(21) Appl. No.: 10/628,315

(22) Filed: Jul. 28, 2003

(65) Prior Publication Data

US 2008/0140194 A1 Jun. 12, 2008

Related U.S. Application Data

(63) Continuation of application No. 09/906,366, filed on Jul. 16, 2001, now abandoned.

(51) Int. Cl.
*A61F 2/12* (2006.01)
(52) U.S. Cl. .............................. 623/7; 450/81
(58) Field of Classification Search ................. 623/7–8; 450/57, 81
See application file for complete search history.

(56) References Cited

U.S. PATENT DOCUMENTS

| | | | |
|---|---|---|---|
| 2,364,866 A | 12/1944 | Meynier, Jr. | |
| 4,199,825 A | 4/1980 | Knoche | |
| 4,227,536 A | 10/1980 | Shimenkov et al. | |
| 4,333,471 A | 6/1982 | Nakai | |
| 4,356,573 A * | 11/1982 | Knoche | 623/7 |
| 4,640,288 A | 2/1987 | Hattori | |
| 4,778,465 A | 10/1988 | Wilkins | |
| 4,870,977 A | 10/1989 | Imonti | |
| 5,171,321 A * | 12/1992 | Davis | 623/7 |
| 5,782,672 A * | 7/1998 | Woodley | 450/57 |
| 2004/0010311 A1* | 1/2004 | Reynolds et al. | 623/7 |
| 2004/0143325 A1* | 7/2004 | Holmes | 623/7 |
| 2004/0143326 A1* | 7/2004 | Holmes | 623/7 |
| 2005/0037689 A1* | 2/2005 | Gorski et al. | 450/81 |
| 2006/0052033 A1* | 3/2006 | Foley et al. | 450/37 |
| 2006/0089084 A1* | 4/2006 | Dohan | 450/81 |

* cited by examiner

*Primary Examiner*—Suzette J Gherbi
(74) *Attorney, Agent, or Firm*—Fitch, Even, Tabin & Flannery

(57) ABSTRACT

A non-surgical device used to duplicate a protruding or non-protruding nipple and areola containing sebaceous glands (Montgomery follicles) and sweat glands, creating the most natural-looking nipple and areola possible. The device will function as a nipple prosthesis, nipple enhancer or a nipple protector. At the user's discretion, the vertex can be shaped in several polyhedral angles, such as rounded, squared and pointed. The nipple portion may be custom sized by cutting for either erect, non-erect, rounded, squared or have a pointed look or it may be left in its original size.

17 Claims, 5 Drawing Sheets

Figure 7
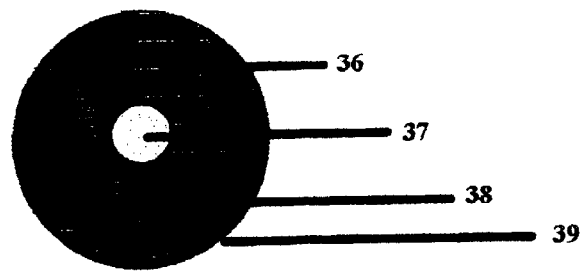
Figure 8
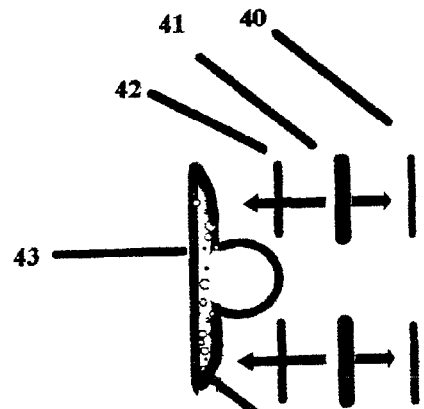
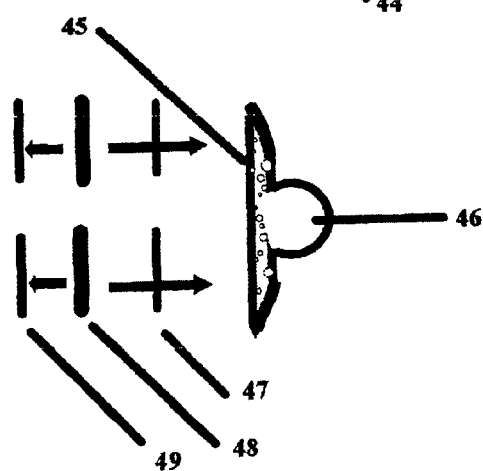
Figure 8A

ADJUSTABLE AREOLA AND NIPPLE PROSTHESIS

This is a continuation, of prior application Ser. No. 09/906,366, filed Jul. 16, 2001, now abandoned which is hereby incorporated herein by reference in its entirety.

BACKGROUND OF THE INVENTION

The present invention creates a device which duplicates a protruding or non-protruding nipple, areola with sebaceous glands (Montgomery follicles) and sweat glands and is non-surgical.

Mainly due to breast cancer, which can lead to a mastectomy (removal of the breasts, nipple and areola), women may choose to have breast reconstruction which may or may not include reconstructing the nipple. Others may have a Mastopexy (or breast lift) which consists of relocating the nipple, creating permanent scar tissue damage and abnormal looking nipples. The device will allow women to have the appearance of a nipple with areola, sebaceous glands (Montgomery follicles) and sweat glands. It will appear natural visually and to the touch with or without clothing on. The customized nipple and areola will allow the user to hide any scar tissue by having a wider areola area that will be undetected by the eye and give the appearance of a natural nipple and areola. In some cases with a mastectomy the only way to duplicate a nipple and areola on a reconstructed breast is through tattooing in which you only have the breast surface to tattoo onto. The device will allow a user to have a natural protruding nipple. This will allow the confidence needed to wear certain clothing (or even go without clothing), without it being detected by the eye or even to the touch. The device can be used to protect the nipple from friction after a surgical procedure whereas the user's own nipple is extremely sensitive, or if the nipple is left permanently sensitive.

Other persons may be born with birth defects such as inverted nipples and areola. Some are born without nipples or the areola area. This device, nipple and areola with all of the joint components of a real nipple, will allow the user to have the natural appearance of a real nipple and areola in an erect or non-erect state.

Males can use the device if in fact they were born with a birth defect such as no nipples and areola or abnormal nipples and areola and would like to look as normal and natural as possible with or without clothing on.

Transsexuals and transvestites may want the appearance of a more feminine erect or non-erect nipple without the dangers of any costly surgery and unpredictable outcome of the appearance of the new nipple. The device will give them the appearance of the most natural-looking nipple and areola with or without clothing.

Surgically-enhanced nipples are very costly and dangerous with uncertainty of the outcome. The device will provide the same appearance of a real nipple visually and to the touch. In most cases they will appear much more pleasant and sexually appealing than the user's real nipple. The device will be light in weight and comfortable to wear. The material used in the device will be resilient and non-absorbing. The device will naturally conduct bodily heat therefore feeling as natural to the touch.

Some women may not choose to surgically enhance their nipples and areola because of the fact that it might affect their ability to breast feed an infant. With the device women can enhance their nipples without affecting any current or future needs to breast feed an infant. Women will not suffer from any loss of sensitivity within their own nipple as with surgery, yet have the appearance of the perfect nipple, without a surgical procedure.

The device of the most natural-looking custom-sized nipples will give all of the users the confidence they need to look natural and more sexually appealing to others. Because the nipples are so natural they can be worn and undetected visually or touch that the user was not born with these perfect natural nipples.

Reference U.S. Pat. No. 5,171,321: the device described in this patent application will benefit over U.S. Pat. No. 5,171,321 is as follows;

The natural nipple of the user varies in size. The natural areola of a user can range in size and shape. The areola of the device in this application can be custom sized in diameter to the user's discretion. Therefore allowing the user to cover their existing nipple and areola with a precise and custom fit. The users may have had a mastopexy or breast lift, which consists of relocating the nipple and areola leaving scar tissue. The user can custom cut the areola with household scissors leaving the areola larger than the user's areola therefore covering any scar tissue from surgery. The user may have two different size nipples and areola resulting from a surgical procedure, birth defect, breast feeding or age, the device can be custom cut with scissors to create even nipples and areola in size and covering existing abnormal or different size nipples and areola. The user may want a larger areola for cosmetic purposes, our device allows the user to determine the areola size of their choice by custom cutting with household scissors. Reference FIG. 1 describing the custom cutting of the device, areola portion. The device description in U.S. Pat. No. 5,171,321 has a disadvantage whereas no custom cutting is allowable. Our's benefits a wider range of users.

Reference U.S. Pat. No. 5,171,321 describes the nipple of the device described in this patent application, the nipple can be custom sized in height with household scissors. The nipple can be custom shaped as described in FIGS. 4 and 5. The U.S. Pat. No. 5,171,321 does not allow for any custom sizing or shaping of the nipple portion. The user may want the nipple to have the appearance of a non-erect, erect, rounded, square or pointed nipple. With household scissors the user can achieve the appearance of the nipple at their discretion and gives the user confidence while wearing the device.

Reference U.S. Pat. No. 5,171,321 describes adhesive affixed to the inner concave surface which in fact limits its use. In this patent application we may provide adhesive circles as described in FIGS. 6, 7 and 8. The adhesive circles has adhesive on both sides similar to double-sided tape. This allows the user to place the adhesive on the inner concave of the device and attaching to the user's breast, chest, nipple, synthetic breast, breast enhancer, breast prosthesis or it can be placed into or on top of a brassiere or any type of clothing or lining of clothing. No relocating of the device will occur. Next the adhesive circles as referenced in FIGS. 6, 7 and 8, can adhere to the top or outer areola of the device in this application allowing the device to adhere to clothing from the top of the device. This would especially benefit a user with sensitive skin whereas the adhesive may irritate the skin of nipple, chest, or breast of the user possibly causing an allergic reaction from the adhesive. Two adhesive circles can be used, placing one on the inner concave surface and the other outer or top of the device allowing the user to adhere the device to the breast as well as a garment or in the lining of clothing. This would provide extra security from the device relocating, this would be especially beneficial while swimming, dancing or during sporting activities where extra movement is accruing The adhesive circles can be custom cut with household scissors to the areola it has been custom cut. The adhesive referenced in U.S. Pat. No. 5,171,321 is preexisting, therefore not allowing the user to select their own adhesive choice, this is critical in user's with sensitive skin where no adhesive can be used. Or where a user can only use a certain based adhesive type. The adhesive circles in the patent application are optional to the user.

Reference U.S. Pat. No. 5,171,321, describes a small grove to duplicate the sebaceous glands (Montgomery follicles) and sweat glands. The sebaceous glands (Montgomery follicles) and sweat glands as described in this patent application are small and subtle bumps which mimic realist sebaceous glands (Montgomery follicles) and sweat glands. Sebaceous glands (Montgomery follicles) and sweat glands are naturally in a rounded form not grooved. The rounder form of the sebaceous glands (Montgomery follicles) and sweat glands gives the appearance of a natural areola, this would benefit the user that wants natural-looking nipples and areola.

Reference U.S. Pat. No. 5,171,321, the device has a hole disposed longitudinally throughout the nipple portion, the nipple portion of the device described in this application is solid throughout allowing for a more realistic appearance of a natural nipple. After custom cutting and shaping the nipple portion of this device as described in FIGS. 4 and 5, the nipple will appear as natural visually and to the touch. The nipple will be colored throughout the inter nipple portion to match the exterior of the nipple and areola The nipple in this patent application will benefit the user over a nipple with a hole in the nipple giving the user a realistic looking nipple and areola.

Reference U.S. Pat. No. 5,171,321, the device has an indentation on the tip surface of said nipple portion, the device described in this patent application will be smooth therefore even if the user does not want to custom cut and shape the nipple portion, the device will have the appearance of a natural nipple visually and to the touch. Natural nipples do not have an indentation, thus the device described in this patent application will benefit over U.S. Pat. No. 5,171,321 providing the user with a realistic nipple protrusion.

Reference U.S. Pat. No. 5,171,321, the device described in this patent application whereas the nipple portion can be custom cut or eliminated. The user may want a smooth appearance if they have naturally protruding nipples they can custom cut the nipple portion and eliminate the nipple completely. This would benefit the user while wearing any garment of clothing including a bathing suit or evening gown where a brassier can not be worn. Or with a scar type of brassier where the user's nipple may protrude thus giving the user a smooth appearance and the needed confidence to wear certain garments. The user may want a protective cover to eliminate any chaffing caused by a garment. This would benefit a user while extra activity is occurring such as aerobic, sporting activities and dancing. Giving the user a wider range of use from no nipple appearance, to non-erect, to erect to no protruding nipple. The device described in U.S. Pat. No. 5,171,321 would not allow the user to eliminate the protruding nipple portion due to the fact that it has a hole disposed longitudinally throughout the nipple portion.

Reference U.S. Pat. No. 4,227,536, the device describes the nipple portion having pins inserted into the nipple to provide positioning of the nipple allowing the nipple portion to be bent upward or straight forward. The nipple portion as described in this patent application can be positioned by using the adhesive circles and applying the device on the existing nipple, chest, etc. or above the nipple or in a higher position to give the appearance of a breast that is firm and high thus achieving better positioning of the device. A disadvantage to the inserted pins, the nipple portion cannot be custom cut and shape to the user's discretion. The height as well can be cut to the user's discretion.

Reference U.S. Pat. No. 4,227,536, the nipple portion is described to be hollow. The device as described in this patent application is the nipple portion is solid throughout and the color is the same throughout thus having a solid nipple the user can custom size and shape the nipple as described in FIGS. 4 and 5. The nipple portion described in this patent application is solid throughout, with the color throughout the nipple portion as well, this benefits the user allowing the custom cutting of the nipple height and nipple shaping. The device described in U.S. Pat. No. 4,227,536 is hollow therefore no custom cutting can be achieved.

Reference U.S. Pat. No. 4,227,536, the device described in this patent application whereas the nipple portion can be custom cut or eliminated The user may want a smooth appearance if they have naturally protruding nipples they can custom cut the nipple portion and eliminate the nipple completely. This would benefit the user while wearing any garment of clothing including a bathing suit or evening gown where a brassier cannot be worn. Or with a scar type of brassier where the user's nipple may protrude thus giving the user a smooth appearance and the needed confidence to wear certain garments. The user may want a protective cover to eliminate any chaffing caused by a garment. This would benefit a user while extra activity is occurring such as aerobic, sporting activities and dancing giving the user a wider range of use from no nipple appearance, to non-erect, to erect. In U.S. Pat. No. 4,227,536, the nipple portion cannot be eliminated due to the fact that the nipple portion has pins in it, the pins would protrude if any cutting was done therefore limiting its use of a nipple cover to provide a smooth appearance while in clothing.

Reference U.S. Pat. No. 4,778,464, describes a surgically-implanted nipple and areola, which must be implanted by a surgeon, thus being costly and unpredictable outcome of surgery. After the nipple and areola is implanted, the users still must apply makeup on the existing skin which will rub off if touched by an article of clothing or skin of another which is impractical. The user can have the skin tattooed which is costly and painful, and still does mimic a natural nipple and areola. If the tattooing is not done to perfection, the user must accept the outcome, therefore still not having a natural-looking nipple and areola. The device in this patent application will give the user the most natural-looking nipple and areola in a painless, non-premeditate manner. The user can wear the device described in this patent in a long-term situation and remove only for hygiene purposes. The device can be easily cared for using soap and water to clean. The device will be made of a resilient material.

SUMMARY OF THE INVENTION

The purpose of the device is to provide the user with a protruding or non-protruding nipple and areola with sebaceous glands (Montgomery follicles) and sweat glands. The nipple, areola and sebaceous glands (Montgomery follicles) and sweat glands will be a joint component. The areola of the device will be thin and flexible to contour to the user's existing nipple, chest, breast, breast prosthesis, breast enhancer or brassier. The inner concave surface can adhere to the user even if there is no existing nipple and areola, due to the fact that it is thin and flexible. The device can be placed inside the lining of clothing. The device is unique because it can be custom sized and shaped providing a custom fit. The appearance will be determined at the user's discretion. This unique custom shape can be achieved by cutting the device with a pair of household scissors, the user is able to accomplish a customized fit. The sebaceous glands (montgomery follicles) and sweat glands will be small and round in size to allow for minimal texture and allow for an appearance to mimic an erect or non-erect nipple state.

The areola portion of the device will be about ½" to 3" in diameter. The nipple portion of the device will be about ¼" to 1" in height. The nipple portion will be solid throughout as well as colored throughout.

The areola will have the appearance of montgomery follicles (or protruding small bumps) to imitate the follicles with a natural nipple color and may be available in colors the would range from Caucasian and/or women of color. The device may be available in novelty colors such as: neon, blue, pink, yellow, orange, translucent, etc. The device may be flavored, edible, or scented.

The areola will be the size that enables the user to achieve a customized fit or leave the device in its original state. The areola of the device will have custom cut lines, thus allowing the user to have a guide when custom sizing the areola to the user's specifications. The user can also cut the device to their own measurement, not relying on the custom cut lines. The vertex can be shaped in several polyhedral angles, such as rounded squared and pointed. The nipple will be raised enabling the user to shape the nipple's height or to shape an erect, non-erect, rounded, squared or pointed nipple. The nipple will be solid with a color throughout, will be self healing when cut thus giving the users the confidence they need to look and feel their best.

The purpose of the device can be used by anyone who had breast cancer, which leads to a mastectomy (or removal of the breast, nipple and areola), a Mastopexy (or breast lift—which consists of relocating the nipple and areola) and anyone who has had a breast reduction, which the nipple and areola are relocated. These individuals are great candidates to use the device to replace existing nipples, enhance existing nipples, or allow them to have natural-looking nipples with all the joint components including a nipple, areola and sebaceous glands (Montgomery follicles) and sweat glands. The device can be used to protect the nipple from friction after a surgical procedure whereas the user's own nipple is extremely sensitive, or if the nipple is left permanently sensitive.

The purpose of the device is that it is functional and can provide anyone with two natural-looking, erect or non-erect nipples. The device will naturally conduct bodily heat therefore feeling as natural to the touch.

The device can be used by anyone who may have had breast cancer, which leads to a mastectomy (or removal of the breast, nipple and areola), whereas one breast has been removed the user may only need to enhance one nipple. Therefore one device can be used to duplicate the user's own existing nipple by custom shaping the nipple and areola of the device and therefore have the appearance of a natural nipple. The device will be light in weight and comfortable to wear.

The device can be used as a novelty item or for entertainment purposes, may be available in novelty colors such as: neon, blue, pink, yellow, orange, translucent, etc.

The device will be easy to care for, cleaning with soap and water.

The user can be male or female. The male user may be a transsexual or a transvestite, the device will give the appearance of a more feminine nipple and areola whether in an erect or non-erect state. The male user may have been born with a birth detect whereas one or both nipples and areola are non present thus allowing a male to have nipples and areola while swimming, sunbathing, or going without a shirt.

The user can wear the device with or without clothing and they will appear natural visually and to the touch. The device will be visually undetectable. The device will be undetectable by touch. The device will be undetectable by scent if the device the user wears is unscented.

The device will give the appearance of more sexually-looking nipples and areola.

The device can be worn in the nude while sunbathing to provide natural-looking nipples with an areola. They will protect the 'real' nipple from sun damage.

The device can be used by the many women who experience uneven nipples in height to the other nipple and areola width size to the other nipple, after nursing a baby or from birth, the device will allow a woman to have even nipples and areola in size.

The device can be custom cut to cover any scars or scar tissue from surgical procedures caused from a breast mastectomy, reconstruction, mastopexy, or reduction. The device can be used to enhance abnormal nipples and areola caused from any surgical procedure, birth, breast feeding or aging.

The user may went to cover their existing nipples from protruding in a bathing suit or evening gown or any garment of clothing were a brassier can or can not be worn, the nipple portion of the device can be custom cut to eliminate any protruding nipple and act as a nipple cover. The user may went a smooth appearance in a garment of clothing and eliminate the nipple completing by custom cutting the device and eliminating the nipple portion thus the device acts as a nipple and areola cover.

The device will prevent nipple friction causing chaffing when worn with clothing, sports wear and sports gear. The device will prevent nipple chaffing when the user has sensitive nipples and areola caused from breastfeeding. The device will prevent nipple chaffing when extra activity is occurring as in aerobic, sporting activities and dancing. The user may have sensitive nipples and areola and require extra protection from chaffing, this device will benefit.

The device will be used as a nipple enhancer and a nipple replacement, nipple prosthesis, if no nipple reconstruction has been performed after a breast reconstruction surgery of any type. Or if the user's nipple will not go into an erect state before or after any type of surgery, the user can have the appearance of an erect nipple with all of the joint components including the sebaceous glands (Montgomery follicles) and sweat glands.

An instruction manual may be available to show the user how to customize the device's nipple size, nipple shape and areola circumference at the user's discretion. The device's position will be determined at the user's discretion. Some users prefer a higher positioned nipple, while others prefer the nipple to be positioned forward or positioned lower with the appearance of a rounded, squared or pointed nipple tip. While the device is adhered to the user's breast, the breast and the device will move up and down as would a natural nipple. Also transversely with other muscles of the body as if it were a real or natural nipple and areola.

The device can be attached to a synthetic breast, breast enhancer or breast prosthesis which allows a woman without a breast to look as natural as possible.

The device can be attached directly to an existing nipple or to skin, where there is no existing nipple or for positioning purposes.

The device can be used for novelty purposes. Allowing a unique and custom sizing that can be used by actors, actresses, nude or exotic dancers or show girls. Tight-fitting clothing can be worn and the nipple will look natural, no brassier will be necessary. The device while used in the nude will give the appearance of erect, non-erect nipples and areola to the user's discretion, a sexual or non sexual natural looking nipple and areola.

The device can be pierced omitting the risk of the user piercing their own nipple and creating permitted damage. The nipple protrusion is a solid object therefore in the event of an accidental puncture by a pin or an intentional puncture by an earring no leaking of fluid will occur or cause the device to weaken in structure.

The device will be available to the public without a doctor's prescription, allowing an economical way to replace or enhance the nipple and areola.

The device can be removed easily at the user's discretion, in a non-surgical manner. The device can be worn in a long-term situation and be removed for hygiene purposes.

The device is a reusable product not a consumable product therefore it will be more economical to the user. The material used in the device will be resilient and non-absorbing.

The device when in use it may give the illusion of larger breasts without surgically altering the user's breast.

The device can enhance the user's nipples and areola without a surgical procedure which can be dangerous, costly and the unpredictable outcome of any surgical procedure.

The device can enhance the user's nipples and areola without affecting the user's ability to breast feed an infant as would a surgical procedure.

The device may be constructed of a material consisting of one of a combination of materials: Petrochemicals, Thermoplastics, Latex-Plastics, Rubber, Foam Rubber, Silicone, Vinyl-PVC, Woven Materials, Fabric, Textiles, Paper Goods, Natural Latex, Acrylates Copolymer, Triethanolamine, Propylene, Clycol, Diazolidnyl Uera, Methylparaben, Propylparaben, Polyesters, Cellulosic, Derivative Materials, Fluorinated Polymers, Epoxies, Phenolics, Collagen, Hydrogels, Elastic and Vulcanized Rubber.

Adhesive circles may be available with the device. The adhesive circles will have adhesive on both sides with a peel-off protective covering allowing the user to adhere the device from the inner concave surface, the top of the device or both for added security while swimming, dancing, aerobic or sporting activities.

The adhesive circles can be custom cut to the custom size of the device's areola therefore no overlapping of adhesive will occur and damage clothing. The adhesive circles will be about ½" to 3" in diameter. The adhesive circles will have a hole in the center thus allowing the nipple portion of the device to protrude through the adhesive circle while applied attopically.

The device can be worn attached to clothing (Bra, Swimsuit, Dress, Sports Wear, etc.) by using the included adhesive circles either on the inside of outside of the device. The user may elect to use their own adhesive choice adhesive similar to but not limited to: Band-Aid® brand, eyelash adhesive, It-Stays® roll on body fixative. Custom cut to fit areola of the device. Applied at the user's discretion, to make the product adhere for a more permanent affect in clothing or on user's chest, nipple, synthetic breast or breast enhancer or breast prosthesis. The user may elect to not using any adhesive, this would benefit in a case where the user has sensitive nipples or skin and an allergic reaction may offer. The user may elect to place the adhesive circles on the top of the device then adhering to an article of clothing thus eliminating any sensitivity to the user nipple, areola or skin eliminating any allergic reactions or skin irritations.

The adhesive may be flavored, edible, or scented.

The adhesive circles may be waterproof. This eliminates any relocating of the device while swimming or bathing.

The materials used in the adhesive for the adhesive circles may consist of one of a combination of the following materials: Natural latex, acrylates, copolymer, triethanolamine, propylene, glycol, diazolidinyl urea, methylparaben, propylparaben.

The materials used in the peel-off protective cover may be made of materials used in the peel-off protective cover on the adhesive circles may consists of one of a combination of the following materials: Petrochemicals, Thermoplastics, Latex-Plastics, Rubber, Foam Rubber, Silicone, Vinyl-PVC, Woven Materials, Fabric, Textiles, Paper Goods, Natural Latex, Acrylates Copolymer, Triethanolamine, Propylene, Clycol, Diazolidnyl Tjera, Methylparaben, Propylparaben, Polyesters, Cellulosic, Derivative Materials, Fluorinated Polymers, Epoxies, Phenolics, Collagen, Hydrogels, Elastic and Vulcanized Rubber.

DESCRIPTION OF THE DRAWINGS

FIG. 7 illustrating the adhesive circle illustrated in a front elevation.

FIG. 8 Illustrating the adhesive circle applied to the top of the areola illustrated in a side view.

FIG. 8A illustrating the adhesive circle applied to the thin and flexible inner surface of the device, illustrated in a side view.

DETAILED DESCRIPTION OF THE INVENTION

Figure 1:
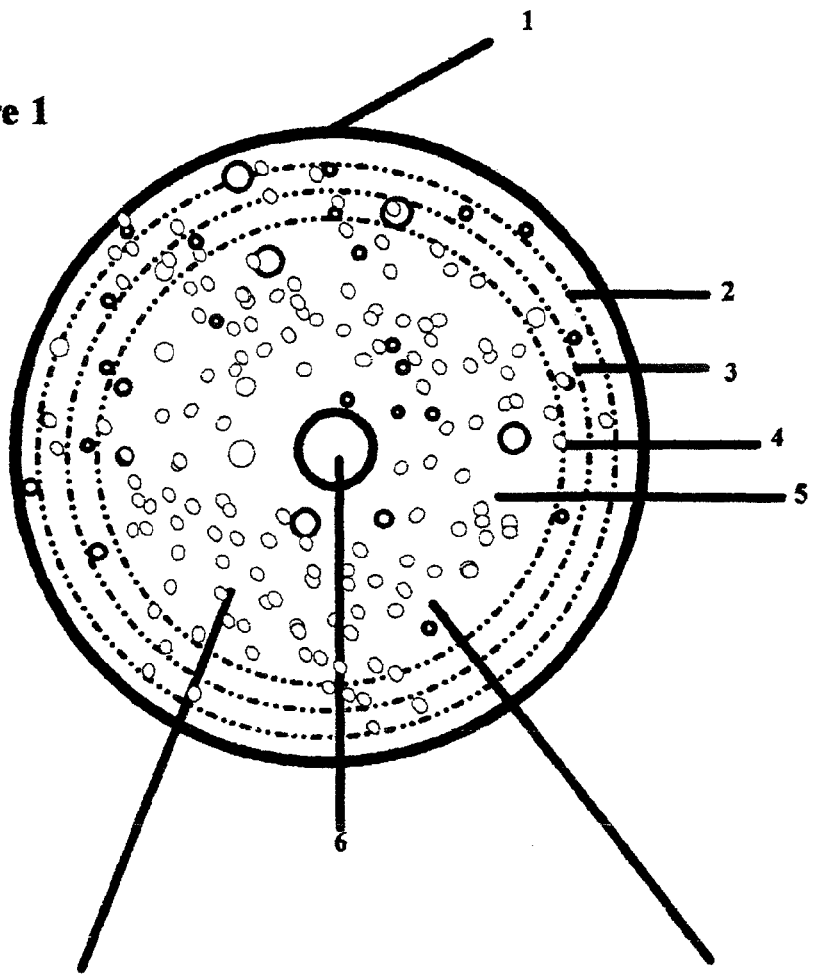
FIG. 1 Illustrating the custom cutting of the areola of the device. Device illustrated in a Front Elevation View.

Referring now in detail of the drawings or figures wherein like parts are designed by like reference numerals throughout.

The device may be made to look like a natural nipple and areola with sebaceous glands (Montgomery follicles) and sweat glands. The nipple areola, sebaceous glands (montgomery follicles) and sweat glands will be formed as a joint component and may be made of one or a combination of the following materials: Petrochemicals, Thermoplastics, Latex-Plastics, Rubber, Foam Rubber, Silicone, Vinyl-PVC, Woven Materials, Fabric, Textiles, Paper Goods, Natural Latex, Acrylates Copolymer, Triethanolamine, Propylene, Clycol, Diazolidnyl Uera, Methylparaben, Propylparaben, Polyesters, Cellulosic, Derivative Materials, Fluorinated Polymers, Epoxies, Phenolics, Collagen, Hydrogels, Elastic and Vulcanized Rubber. Reference FIGS. 1-8A including numerals 1-49.

The areola will be made in a diameter of about ½" to 3" inches. The areola will be thin and flexible therefore it may be custom cut to the individual size and shape for comfort and ease of wearability by the user.

The areola of the device will have custom cut lines, thus allowing the user to have a guide when custom sizing the areola to the user's specifications. The user can also cut the device to their own measurement, not relying on the custom cut lines.

The nipple will be about ¼" to 1" in height and may be custom cut and custom shaped to the exact height and shape preferred by the user.

Since all breasts, nipples and areola are different in size, the user may custom cut and shape the areola and nipple to his/her personal size and/or preference.

Included with the device may be a double-sided adhesive circles made of one or a combination of these materials: Petrochemicals, Thermoplastics, Latex-Plastics, Rubber, Foam Rubber, Silicone, Vinyl-PVC, Woven Materials (Fabric/Textiles), Paper Goods, Natural Latex, Acrylates Copolymer, Triethanolamine, Propylene, Clycol, Diazolidnyl Uera, Methylparaben, Propylparaben, Polyesters, Cellulosic, Derivative Materials, Fluorinated Polymers, Epoxies, Phenolics, Collagen, Hydrogels, Elastic and Vulcanized Rubber. The adhesive circle will have a covering to protect adhesive made of one or a combination of these materials: Petrochemicals, Thermoplastics, Latex-Plastics, Rubber, Foam Rubber, Silicone, Vinyl-PVC, Woven Materials, Fabric, Textiles, Paper Goods, Natural Latex, Acrylates Copolymer, Triethanolamine, Propylene, Clycol, Diazolidnyl Uera, Methylparaben, Propylparaben, Polyesters, Cellulosic, Derivative Materials, Fluorinated Polymers, Epoxies, Phenolics, Collagen, Hydrogels, Elastic and Vulcanized Rubber. The adhesive circle will allow the user to adhere the device to his/her own chest, breast, nipple, synthetic breast or breast enhancer. Or to adhere the device to clothing either from the inside of the device or from the outside of the device. The adhesive circle may be custom cut to adhere to the top of the areola of the device or the thin and flexible inner surface of the device. The adhesive circle will be about ½" to 3" with a hole in the center, allowing the nipple of the device to protrude through the adhesive circle when adhered to the device on the top portion of the areola as illustrated in FIGS. 8 and 8A.

The user may select to use their own adhesive and it may be similar to: Band-Aid® brand, eyelash adhesive, It-Stays® roll on body fixative and it may be waterproof.

FIG. 1 Illustrating the Custom Cutting of the Areola of the Device. Device Illustrated in Front Elevation View.

The device as illustrated in FIG. 1 consists of an areola 1, a nipple 6, sebaceous glands (Montgomery follicles) and sweat glands 5, custom cut lines 2, 3, 4, as a joint component.

Reference FIG. 1, the areola 1 will have natural-looking sebaceous glands (Montgomery follicles) and sweat glands 5, the areola 1 will be about ½" to 3" in diameter and allow the user to custom fit the areola 1 to the user's personal preference using a custom cut lines 2, 3, 4. Describing the custom cut 2, 3, 4 of the areola 1, the user can leave the device at its original size 1 to cover scars on their own breasts or chest or for personal preference size of a large areola. The user can custom cut 2, 3, 4 the areola 1 using the guided cut lines or custom cut the areola to any size the user desires for personal fit and comfort. The custom cutting 2, 3, 4 of the areola 1 will be achieved by using household scissors and a user's guide.

The size of the custom cuts can vary by the user, thus for personal sizing requirements cutting more or less as so desired The end result being a perfect sizing of the areola using the custom cutting feature.

After the device has been custom cut 2, 3, 4 from the original size 1, the sebaceous glands (Montgomery follicles) and sweat glands 5 will not be affected by any custom cutting due to the fact that they are subtle and not overly large, the texture and color will be the same as the joint component of the nipple and areola. Giving the user the most natural-looking areola 1 to the eye and to the touch.

The areola 1 will be thin and flexible. The sebaceous glands (Montgomery follicles) and sweat glands 5 will be slightly raised.

Figure 2:
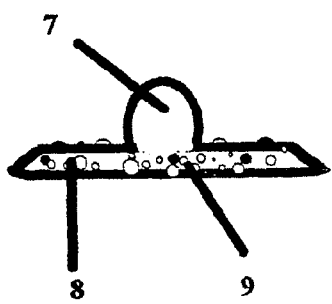
FIG. 2 Illustrating the sebaceous glands (montgomery follicles) and sweat glands of the Device. Device illustrated in a side view.

FIG. 2 Illustrating the Sebaceous Glands (Montgomery Follicles) and Sweat Glands of the Device. Device Illustrated in a Side View.

Reference FIG. 2, illustrating the sebaceous glands (Montgomery follicles) and sweat glands 8 of the device, whereas the areola 9, the nipple 7 and the sebaceous glands (Montgomery follicles) and sweat glands 8 will be a joint component. The sebaceous glands (Montgomery follicles) and sweat glands 8 being slightly raised and soft in texture, the color will be the same as the joint component of the Device. The sebaceous glands (Montgomery follicles) and sweat glands 8 will vary in size and shape as would natural sebaceous glands (Montgomery follicles) and sweat glands.

Figure 3:
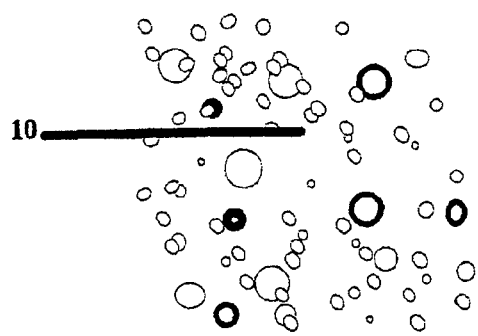
FIG. 3 Illustrating the sebaceous glands (Montgomery follicles) and sweat glands. Device shown in a front elevation.

FIG. 3 Illustrating the Sebaceous Glands (Montgomery Follicles) and Sweat Glands. Device Illustrated in a Front Elevation.

Reference FIG. 3, the sebaceous glands (Montgomery follicles) and sweat glands 10 will be slightly raised and soft in texture, the color will be the same as the joint component of the Device. The sebaceous glands (Montgomery follicles) and sweat glands 10 will vary in size and shape as would natural sebaceous glands (Montgomery follicles) and sweat glands.

Figure 4:
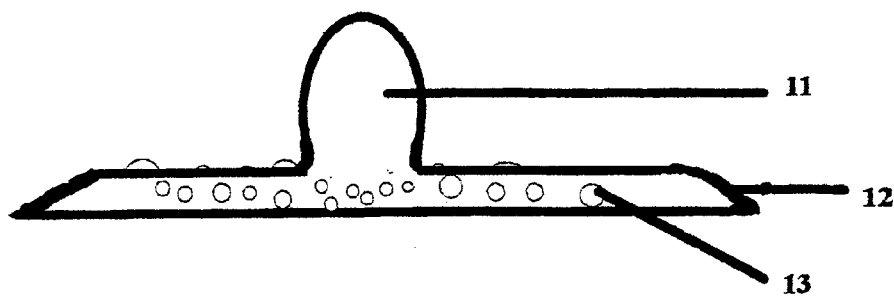
FIG. 4A-D illustrating the custom cutting and shaping of the nipple of the Device. Device illustrated in a side view.
Figure 4A:
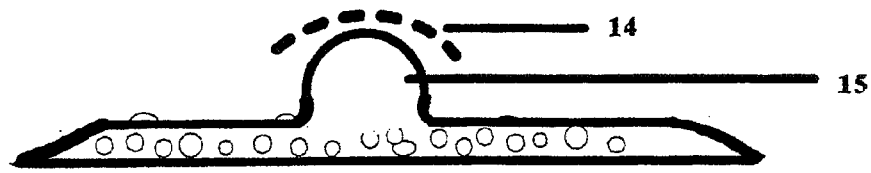
Figure 4B:
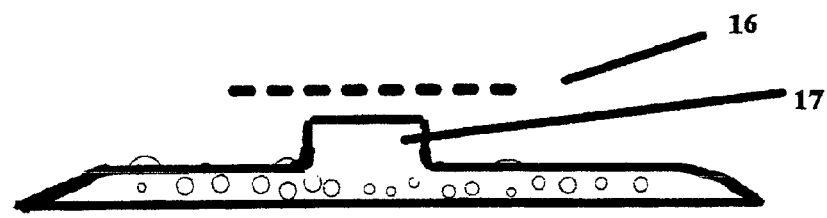

FIG. 4A—Illustrating, the Custom Cutting and Shaping of the Nipple of the Device. Device Illustrated in a Side View.

Reference FIG. 4, illustrating the device as a joint component consisting of a nipple 11, areola 12 and sebaceous glands (Montgomery follicles) and sweat glands 13 in its original size of the nipple 11 about ¼" to 1" in height and the areola 12 in size from about ½" to 3" in diameter. The user may want to use the device to enhance their sexuality by having a large, erect nipple 11, therefore the user may want the nipple 11 to remain in its original height.

As illustrated in FIG. 4A, the user may prefer a smaller nipple 15 therefore custom sizing the height of the nipple 15. The user may prefer the appearance of a rounded nipple 15 tip therefore custom shaping 14 the nipple 15 to a rounded formation. This may be done with household scissors and a user's manual. The nipple will have the appearance of a natural nipple 15. The nipple 15 will be solid and color will be throughout the nipple 15. The nipple 15 will be self healing after custom cutting and shaping 14. The color of the device may be colored to match the color of Caucasian and/or women of color. The device may be available in novelty colors such as: neon, blue, pink, yellow, orange, transparent, etc.

As illustrated in FIG. 48, the user may prefer a nipple 17 with a squared appearance, the user can custom cut 16 the nipple 17 thus custom shaping 16 the nipple 17 into a squared formation. This may be done with household scissors and a users manual. The nipple 15 will be solid and color will be throughout the nipple 17. The nipple 17 will be self healing after custom cutting and shaping 16. The color of the device may be colored to match the color of Caucasian and/or women of color. The device may be available in novelty colors such as: neon, blue, pink, yellow, orange, transparent, etc.

Figure 4C:
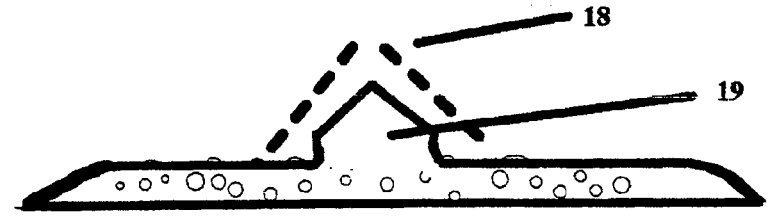

As illustrated in FIG. 4C, the user may prefer a nipple 19 with a pointed appearance, the user can custom cut 18 the nipple 19 thus custom shaping 18 the nipple 19 into a squared formation. This maybe done with household scissors and a users manual. The nipple 19 will be solid and color will be throughout the nipple 19. The nipple 19 will be self healing after custom cutting and shaping 18. The color of the device may be colored to match the color of Caucasian and/or women of color. The device may be available in novelty colors such as: neon, blue, pink, yellow, orange, transparent, etc.

Figure 4D:
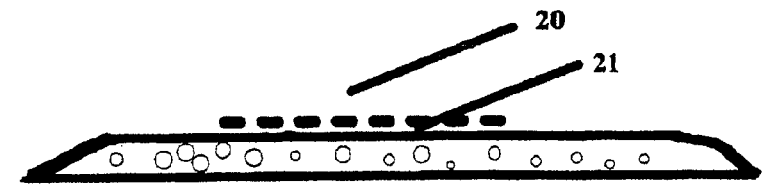

As illustrated in FIG. 4D the nipple 21 can be custom cut 20 to eliminate the nipple 21 therefore no nipple will be present and the device can act as a nipple cover to eliminate protruding nipples thus giving the user a smooth appearance.

FIG. 5A-D Illustrating the thin and flexible inner surface of the device attached to a breast. Device illustrated in a side view Reference FIG. 5, the device shown in a side view attached to a breast 22 by the thin and flexible inner surface 26 as a joint component consisting of a nipple 24, areola 23, flexible inner surface 26 and sebaceous glands (Montgomery follicles) and sweat glands 25. The thin and flexible inner surface 26 is shaped to fit on all chests and breasts, whether male or female, to cover existing nipples, chest, breast or synthetic prosthesis without any existing nipples and areola, with comfort and ease of wearability. The device will fit onto an article of clothing or in conjunction within the lining of a brassiere or sportswear. The thin and flexible inner surface 26 may be attached using an adhesive to allow the device to stay in place, or using adhesive circle as illustrated in FIG. 7 that may be water resistant to allow the user to wear the device without the device relocating.

Figure 5:
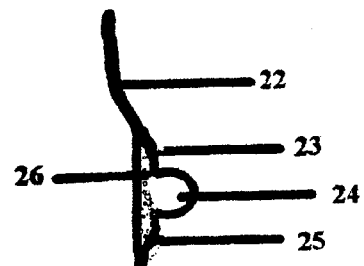
FIG. 5A-D Illustrating the thin flexible inner surface of the device attached to a breast. Device illustrated in a side view.
Figure 5A:
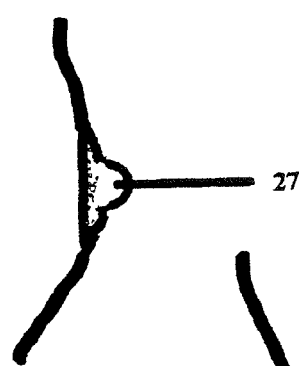

FIG. 5A illustrating the device attached to a breast with a custom cut and shaped smaller, rounded nipple 27.

Figure 5B:
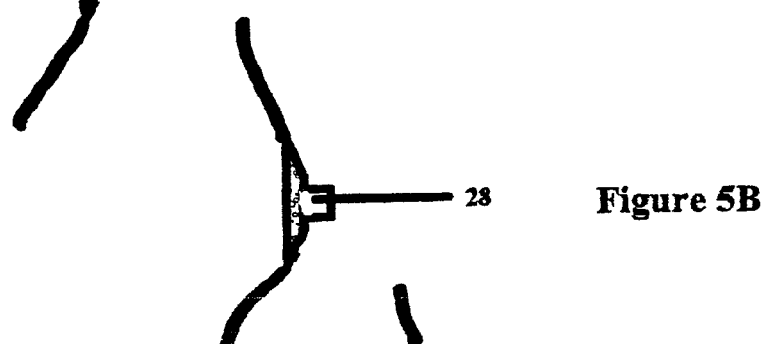

FIG. 5B illustrating the device attached to a breast with a custom cut and shaped squared nipple 28.

Figure 5C:
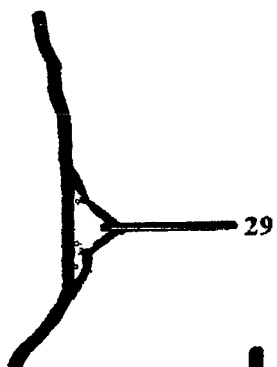

FIG. 5C illustrating the device attached to a breast with a custom cut and shaped pointed nipple 29.

Figure 5D:
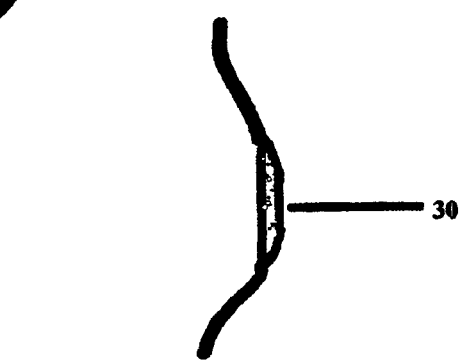

FIG. 5D, illustrating the device attached to a breast after custom cutting the nipple 30 by eliminating the nipple and using the device as a nipple cover.

Figure 6:
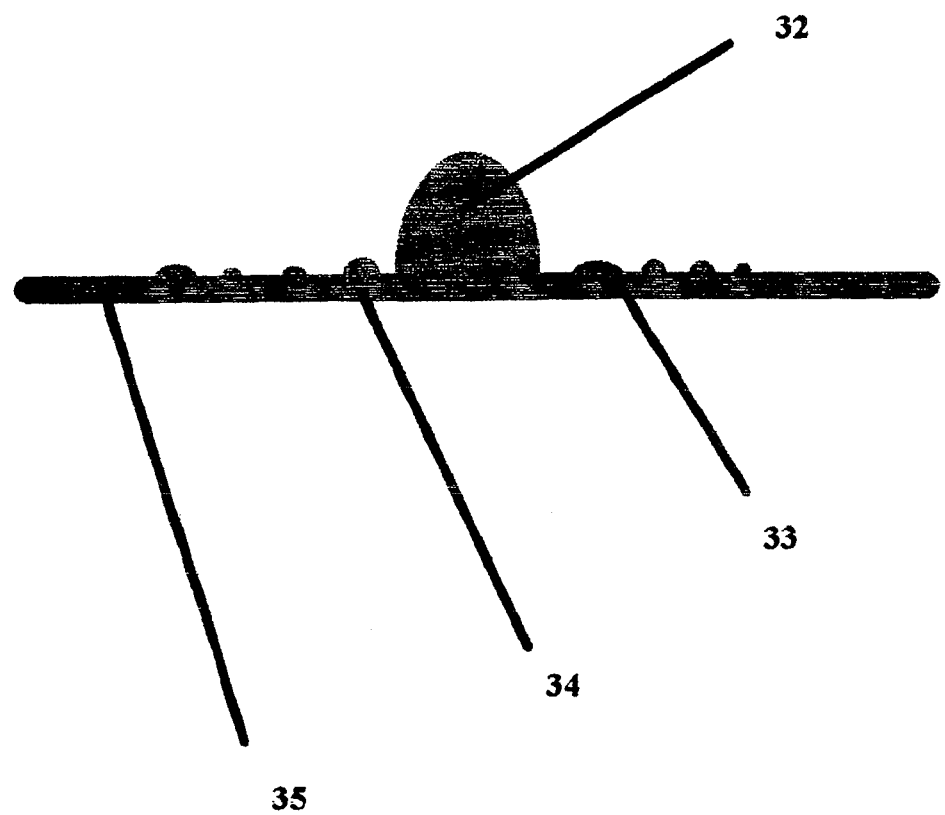
FIG. 6 Mid-Section of the Device. Device illustrated in a side view.

FIG. 6 Mid-Section of the Device. Device Illustrated in a Side View.

Reference FIG. 6, the device shown in a side view as a joint component consisting of a nipple 32, areola 34 with sebaceous glands (montgomery follicles) and sweat glands 33. The device will be a solid object 35, throughout the nipple 32, areola 34 and sebaceous glands (Montgomery follicles) and sweat glands 33. The color will be solid 35 throughout the nipple 32, areola 34 and sebaceous glands (Montgomery follicles) and sweat glands 33. The texture will be throughout the device and will be a culmination of the material used and will mimic the feeling of a natural nipple with regards to the sebaceous glands (Montgomery follicles) and sweat glands on the areola.

The nipple 32 and the areola 34 will be self healing after custom cutting and shaping due to the fact that the device will be a solid 35 object and joint component. The color of the device may be colored to match the color of Caucasian and/or women of color. The device may be available in novelty colors such as: neon, blue, pink, yellow, orange, transparent, etc.

FIG. 7—Illustrating the Adhesive Circle Illustrated as a Front Elevation.

Reference FIG. 7, the front elevation of the adhesive circle 36 which is double-sided adhesive with a cut-out hole 37 in the center, to allow nipple to protrude through when attached to the top of the areola as illustrated in FIG. 8. There will be a peel-off protective cover 38, located on the top of the adhesive circle and a protective peel-off cover 39 located on the bottom of the adhesive circle.

The peel-off protective covers 38, 39 to be removed by user and the user can custom cut using household scissors to fit the custom cut of the areola by user. The adhesive circle 32 will be about ½" to 3" in diameter.

FIG. 8 Illustrating the Adhesive Circle Applied to the Top of the Areola Illustrated in a Side View.

Reference FIG. 8, describing the use of double-sided adhesive circle 41 illustrated in a side view adhering to the top of the areola 44 of the device 43 and showing peel-off protective covers 40, 42. The double-sided adhesive circle 41 when adhered to the top of the areola 44 of the device 43 allows the device 43 to attach to a garment or lining of a garment from the inside. This will be achieved by removing the peel-off protective covers 40, 42 from the adhesive circle 41 and then adhering the adhesive circle 41 to the top of the areola 44 of the device 43. The cut out circle as Reference in FIG. 7 number 37 allows the nipple portion of the device to protrude through the adhesive circle 41.

FIG. 8A—Illustrating the Adhesive Circle Applied to the Thin and Flexible Inner Surface of the Device Illustrated in a Side View.

Reference FIG. 8A describing the use of double-sided adhesive circle 48 illustrated in a side view adhering to the thin and flexible inner surface 48 of the device 46 and showing peel off protective covers 47, 49. The double-sided adhesive circle 48 when adhered to the thin and flexible inner surface of the device 44 allows the device to attach to a natural breast, chest, nipple, synthetic breast, breast enhancer, breast prosthesis or chest whether the user has a flat, small, medium or large breast or chest. This will be achieved by removing the peel-off protective covers 47 and 49 from the adhesive circle 48 and then adhering the adhesive circle 48 to the thin and flexible inner surface 45 of the device 46, then adhering to the user's natural breast, chest, nipple, synthetic breast, breast enhancer, breast prosthesis or chest, as illustrated in FIGS. 5-A-D.

What is claimed:

1. An adjustable areola and nipple prosthesis comprising:
    an areola having an inner concave surface and an outer concave surface, the outer concave surface including a central portion and an exterior portion, said exterior portion containing rounded natural looking sebaceous glands and rounded sweat glands of different sizes, the inner concave surface including an adhesive;
    at least one circular cut line extending around a circumference of the areola; and
    a nipple protruding outwardly from the central portion of the outer concave surface of the areola;
    the areola having an adjustable diameter of from about 0.5 to about 3 inches and the nipple having an adjustable height of from about 0.25 to about 1 inch.

2. The adjustable areola and nipple prosthesis of claim 1, wherein the prothesis is formed of a material selected from the group consisting of petrochemicals, thermoplastics, latex plastics, rubber, foam rubber, silicone, vinyl-PVC, woven material, fabric, textiles, paper goods, natural latex, acrylates copolymer, triethanolamine, propylene, glycol, diazolidnyl urea, methylparaben, propylparaben, polyesters, cellulosics, fluorinated polymers, epoxies, phenolics, collagen, hydrogels, elastic, vulcanized rubber, and combinations thereof.

3. The adjustable areola and nipple prosthesis of claim 1, wherein the adhesive is provided as one or more adhesive circles.

4. The adjustable areola and nipple prosthesis of claim 1 further comprising an adhesive on the outer concave surface of the areola.

5. The adjustable areola and nipple prothesis of claim 1, wherein the prosthesis is made of colored materials.

6. The adjustable areola and nipple prothesis of claim 1, wherein the prosthesis is made of flavored materials.

7. The adjustable areola and nipple prothesis of claim 1, wherein the nipple is square in shape.

8. The adjustable areola and nipple prothesis of claim 1, wherein the nipple is rounded in shape.

9. The adjustable areola and nipple prothesis of claim 1, wherein the nipple is pointed.

10. The adjustable areola and nipple prothesis of claim 1, wherein the nipple is flat.

11. An adjustable areola prosthesis comprising:
an areola having an thin and flexible inner surface and an outer concave surface, the outer concave surface including a central portion and an exterior portion, said exterior portion containing rounded natural looking sebaceous glands and rounded sweat glands of different sizes, the inner concave surface including an adhesive; and
at least one circular cut line extending around a circumference of the areola, the areola having an adjustable diameter of from about 0.5 to about 3 inches.

12. The adjustable areola prothesis of claim 11, wherein the prothesis is formed of a material selected from the group consisting of petrochemicals, thermoplastics, latex plastics, rubber, foam rubber, silicone, vinyl-PVC, woven material, fabric, textiles, paper goods, natural latex, acrylates copolymer, triethanolamine, propylene, glycol, diazolidnyl urea, methylparaben, propylparaben, polyesters, cellulosics, fluorinated polymers, epoxies, phenolics, collagen, hydrogels, elastic, vulcanized rubber, and combinations thereof.

13. The adjustable areola prothesis of claim 11, wherein the adhesive is provided as one or more adhesive circles.

14. The adjustable areola prothesis of claim 11, further comprising an adhesive on the outer concave surface of the areola.

15. The adjustable areola prothesis of claim 11, wherein the prosthesis is made of colored materials.

16. The adjustable areola prothesis of claim 11, wherein the prosthesis is made of flavored materials.

17. A method of enhancing breast appearance, the method comprising:
forming an adjustable areola and nipple prosthesis to a desired size by cutting along at least one circular cut line extending around a circumference of the areola to provide an areola having a diameter of from about 0.5 to about 3 inches;
attaching the adjustable prosthesis using an adhesive, wherein the adjustable prosthesis includes an areola having an inner surface and an outer concave surface, the outer concave surface including a central portion and an exterior portion, said exterior portion containing rounded natural looking sebaceous glands and rounded sweat glands of different sizes and a nipple protruding outwardly from the central portion of the outer concave surface of the areola.

* * * * *